(12) United States Patent
Olsson

(10) Patent No.: US 11,335,212 B2
(45) Date of Patent: May 17, 2022

(54) SURGICAL SIMULATION ARRANGEMENT

(71) Applicant: FOLLOU AB, Torslanda (SE)

(72) Inventor: Fredrik Olsson, Torslanda (SE)

(73) Assignee: FOLLOU AB, Torslanda (SE)

( * ) Notice: Subject to any disclaimer, the term of this patent is extended or adjusted under 35 U.S.C. 154(b) by 406 days.

(21) Appl. No.: 16/604,418

(22) PCT Filed: Apr. 9, 2018

(86) PCT No.: PCT/SE2018/050364
§ 371 (c)(1),
(2) Date: Oct. 10, 2019

(87) PCT Pub. No.: WO2018/190765
PCT Pub. Date: Oct. 18, 2018

(65) Prior Publication Data
US 2020/0202746 A1    Jun. 25, 2020

(30) Foreign Application Priority Data

Apr. 11, 2017  (SE) .................................... 1750434-1

(51) Int. Cl.
*G09B 23/28* (2006.01)
*A61B 34/10* (2016.01)
(Continued)

(52) U.S. Cl.
CPC .............. *G09B 23/28* (2013.01); *A61B 17/00* (2013.01); *A61B 34/10* (2016.02); *A61B 34/76* (2016.02); *G06F 3/016* (2013.01); *A61B 2017/00716* (2013.01); *A61B 2034/101* (2016.02); *A61B 2034/2059* (2016.02)

(58) Field of Classification Search
CPC ....... G09B 23/28; G09B 23/285; G09B 23/30
See application file for complete search history.

(56) References Cited

U.S. PATENT DOCUMENTS 5,805,140 A * 9/1998 Rosenberg ............. G01B 5/008
                                                        345/161
6,024,576 A * 2/2000 Bevirt ...................... G05G 9/04
                                                        345/158
(Continued)

FOREIGN PATENT DOCUMENTS

CN     102622935 B     4/2014
CN     104537938 A     4/2015
(Continued)

OTHER PUBLICATIONS

PCT International Search Report and Written Opinion dated May 7, 2018 for International Application No. PCT/SE2018/050364, 10 pages.
(Continued)

*Primary Examiner* — Kurt Fernstrom
(74) *Attorney, Agent, or Firm* — RMCK Law Group, PLC

(57) ABSTRACT

The present disclosure relates to a surgical simulation arrangement for a user handling a simulation instrument, allowing for simulation improvements when simulating e.g. a laparoscopic, arthroscopic or thoracoscopic procedure. The present disclosure also relates to a haptic user interface device for use with a surgical simulation system.

20 Claims, 5 Drawing Sheets

(51) Int. Cl.
*A61B 34/00* (2016.01)
*A61B 17/00* (2006.01)
*G06F 3/01* (2006.01)
*A61B 34/20* (2016.01)

(56) References Cited

U.S. PATENT DOCUMENTS

| | | | |
|---|---|---|---|
| 6,037,927 A | 3/2000 | Rosenberg | |
| 6,786,727 B2 * | 9/2004 | Irion | G09B 19/24 |
| | | | 434/55 |
| 7,001,330 B2 | 2/2006 | Kobayashi | |
| 7,706,000 B2 * | 4/2010 | Cohen | G09B 23/28 |
| | | | 356/614 |
| 8,764,448 B2 * | 7/2014 | Yang | B25J 7/00 |
| | | | 434/262 |
| 9,827,050 B2 * | 11/2017 | Johansson | G09B 23/285 |
| 10,973,594 B2 * | 4/2021 | Crawford | A61B 34/20 |
| 11,045,267 B2 * | 6/2021 | Hussain | A61B 17/1757 |
| 11,189,195 B2 * | 11/2021 | Munro | G09B 9/00 |
| 2007/0018958 A1 * | 1/2007 | Tavakoli | A61B 34/76 |
| | | | 345/161 |
| 2015/0265140 A1 | 9/2015 | Hafner et al. | |
| 2016/0133158 A1 * | 5/2016 | Sui | G09B 23/285 |
| | | | 434/262 |
| 2018/0366034 A1 * | 12/2018 | Casals Gelp | G09B 23/285 |

FOREIGN PATENT DOCUMENTS

| | | |
|---|---|---|
| DE | 102008013495 A1 | 9/2009 |
| EP | 2738756 A1 | 6/2014 |
| EP | 2760003 A1 | 7/2014 |
| WO | 0237452 A1 | 5/2002 |
| WO | 2005039835 A1 | 5/2005 |

OTHER PUBLICATIONS

Extended European Search Report dated Nov. 19, 2020 for European Patent Application No. 18785081.3, 8 pages.

* cited by examiner

SURGICAL SIMULATION ARRANGEMENT

CROSS-REFERENCE TO RELATED APPLICATIONS

This application is a 371 U.S. National Stage of International Application No. PCT/SE2018/050364, filed Apr. 9, 2018, which claims priority to Swedish Patent Application No. 1750434-1, filed Apr. 11, 2017. The disclosures of each of the above applications are incorporated herein by reference in their entirety.

TECHNICAL FIELD

The present disclosure relates to a surgical simulation arrangement for a user handling a simulation instrument, allowing for simulation improvements when simulating e.g. a laparoscopic, arthroscopic or thoracoscopic procedure. The present disclosure also relates to a haptic user interface device for use with a surgical simulation system.

BACKGROUND

Surgical simulation systems are being more and more used to train a physician in different surgical procedures in a risk-free environment. In particular, in the field of minimal invasive surgery, such as e.g. laparoscopy, arthroscopy etc. the surgical simulation systems have gained a high degree of acceptance. The simulation software has become realistic to such extent that the computer-generated images and the behavior during interaction with the simulator gives a high degree of realism, but there are still elements in the simulation significantly different from reality, and the intention of the present disclosure is to address a few of them which is related to the user interface device.

A simulation system typically comprises a computer with simulation software and a user interface device, which gives the operator a realistic training environment. The user interface device consists of an arrangement that has one or more representations of surgical instruments (hereby referred to as "instruments"), such as graspers, scissors, needle drivers, endoscopes etc. which the operator can manipulate. The instrument movements are being tracked by sensors in the user interface device, and these movements are being sent to the simulation computer where the software uses the angles and positions to create the video corresponding to the poses of the instruments and to create an interaction response, such as deformations of the tissue, guidance, metric calculations etc. Some user interface devices also contain actuators which enables force-feedback to the user. In that case the user interface device is a haptic user interface device. In this case, the simulation software calculates forces and torques based on e.g. collisions or interactions with the tissue. These forces and torques are sent to user interface device, which outputs the corresponding forces and torques to the actuators, and the user gets the sensation that he or she feels the collisions against the geometric representation of the tissue being presented on the screen. Force-feedback provides an additional degree of realism which has proven to give a positive impact on the learning and training. The present disclosure has force feedback and can therefore be referred to as a haptic user interface devices. The implementation of the present disclosure can also be without force-feedback, and therefore, in the following, it will be referred to as the user interface device, which intends to cover both the haptic and the non-haptic implementation.

For e.g. laparoscopy, the user interface device is a relatively complicated arrangement, because it needs to track an instrument in four degrees of freedom, and ultimately (for the haptic interface device) it should also provide force-feedback to all four degrees of freedom. Typically, this arrangement tracks a rigid elongated object, which is a shaft part of the representation of an instrument being used in minimal invasive surgery procedures. For instance, a grasper, which is used to hold or dissect a tissue, can in reality be 5 mm in diameter and roughly 350 mm long. Instruments used in pediatric surgery are much shorter and instruments used with obese patients are much longer.

In reality, a minimal invasive surgical procedure, e.g. a laparoscopic procedure can be performed by using typically 3-4 so called ports, which are tubular devices that are arranged on the patient by penetrating the patient body. The ports give access to the target area inside the patient. Some procedures, typically more complicated ones, uses up to 6 ports. The operators use the ports to gain access from different directions and many ports can be used simultaneously for different tasks. The ports are in some literature referred to as working ports, scope ports and retraction ports. The working ports are the ports from which the main work is performed by e.g. dissecting, cutting, stapling or suturing the tissues. The retraction ports are ports that one or more assistants are using to create a good working space around and access to the procedure target area for the main operator, by e.g. retracting or pushing away an organ. The scope port is used for the laparoscope, which is often manipulated by a dedicated assistant surgeon. During the procedure, a scope portal can become an alternate working portal and vice versa if the access or viewing is judged to be beneficial. A typical surgery team consist of several members, including the main surgeon, assistant surgeon or surgeons, scrub nurses, anesthesiology doctor etc.

In accordance to prior-art in the field of laparoscopic, arthroscopic or thoracoscopic simulation with a pivotally suspended user interface, some haptic, some non-haptic, comprises working stations that consists of a wheeled cart with a computer, a monitor, a keyboard and a set of user interface devices corresponding to a scope portal for the camera instrument, and two working instruments. The scope and instrument have fix positions, meaning that the simulated port positions are fixed and cannot be changed, either as a group or in relation to each other. The scope port is placed between and below (or proximal, in relation to the operator) the instrument ports. The user cannot change the setup and adjust it according to a specific procedure, which has the disadvantage that the training of the procedures doesn't reflect the real life geometrical setup of the ports. And as mentioned above, the real portal setup differs quite much between one procedure and another, and since the programmed exercises in the simulator target many different areas (liver, stomach, spleen, kidneys etc.), the real portal setup and the corresponding simulated portal setup will differ to an extend that the exercise becomes unrealistic for procedures that doesn't reflect the simulator's static setup.

Another shortcoming of the existing solutions is that the instrument shaft is an integral part of the user interface device. The instrument shaft can be moved in the mentioned four degrees of freedom but cannot be pulled out, because there is a mechanical stop that prevents them to. For some of the solutions, the mechanical stop cannot just be removed, because the stop is part of a mechanism for tracking and actuating the shaft lengthwise. The stop can for instance be a holder of a wire that is part of the transmission to the insertion actuator. For other solutions, the shaft is simply prevented to be pulled out by design, because it is too cumbersome for the user to put the shaft back into the tracking/actuating mechanism since the shaft has to be turned to a certain orientation to meet a mechanism. This makes an instrument withdrawal and a following insertion exercise too unnatural and this particular training value would be lost.

Another aspect of the prior-art simulator working stations is that the operator stands next to it in a quite relaxed way because he or she always stands in front of the working portals. From a training perspective, this has two major drawbacks. Firstly, that the user doesn't know how he or she is oriented in relation to the patient and therefore cannot easily understand where the ports are supposed to be for a particular simulation exercise. Secondly, since the user stands next to the simulator in the same way regardless of simulated procedure, he or she doesn't understand the actual limitations when working from a particular position. E.g. the patient arms, legs or body can substantially affect the operators working environment, which in reality adds an extra degree of difficulty that isn't reflected when training on the mentioned simulator workstations.

Accordingly, although the existing laparoscopic simulators are quite well suited for individual training they still lack in realism in the abovementioned aspects, which opens for further improvements that can make both individual and team training more realistic and thereby provide a more powerful educational platform. Thus, there seems to be room for further improvements in relation to haptic user interface devices and surgical simulation systems comprising such haptic user interface devices.

Further attention is drawn to WO2005039835. WO2005039835 disclose a sub-assembly for receiving a laparoscopic instrument, comprising a receptor that is pivotally arranged in a bracket. The receptor in turn comprises an opening for receiving the laparoscopic instrument. The bracket is pivoted at a pin to a post, where an angle between the bracket and the post may be adjusted for the comfort of a user handling the laparoscopic instrument.

SUMMARY

It is an objective of the present disclosure to address the limitations of the prior art, and to provide an improved user interface device which gives a basis for an improved educational platform, by its extended functionality and a size and shape that enables multiple and arbitrary portal setting and integration into or onto a manikin.

According to an aspect of the present disclosure, the above is at least partly met by a surgical simulation arrangement for a user handling a simulation instrument, the surgical simulation arrangement comprising a first elongated portion extending along an instrument longitudinal axis (C) and having a proximal and a distal end, the first elongated portion provided with an instrument passage extending from the proximal to the distal end and adapted for receiving a shaft of the simulation instrument, wherein the instrument passage is adapted to allow the shaft of the simulation instrument to move longitudinally through the instrument passage, a second elongated portion extending along a first axis (A) and having a first and a second end, and a joint arrangement adapted to pivotally connect the distal end of the first elongated portion with the first end of the second elongated portion, wherein the instrument passage is positioned in a direction away from the second elongated portion in relation to the joint.

By means of the structural implementation as is achieved in accordance to the present disclosure, it has shown possible to improve how a surgical simulation set-up may be structured, allowing for multiple portals and variable portal settings, that decouples the instruments from the device, and that allows insertion and full retraction.

The flexibility achieved by means of the present disclosure is made possible by arranging the above mentioned instrument passage in a position away from the second elongated portion in a direction away from the joint. Thus, in operation the second elongated portion is preferably fixed to e.g. a base (structure), and the first elongated portion is movable at the joint. The user may also insert and retract the shaft of the instrument through the instrument passage.

The instrument passage is preferably arranged "within" ("encapsulated within") the first elongated portion, but could in a possible alternative embodiment be arranged also on an "outside of" the first elongated portion. In an embodiment the instrument passage is arranged parallel to the instrument longitudinal axis (C) and adapted to allow the shaft of the simulation instrument to move longitudinally through the instrument passage.

According to another aspect of the present disclosure there is provided a haptic user interface device for a surgical simulation system comprising a frame having a fixed base, a middle portion rotatable around a first axis (A) in relation to the base, and an instrument receiving portion rotatable around a second axis (B) in relation to the middle portion, where the second axis is essentially perpendicular to the first axis, and an instrument representation having a rigid shaft which can be inserted into the instrument receiving portion, along an instrument longitudinal axis (C). When the instrument representation is inserted into the instrument receiving portion it will be constrained to move around the said first and second axis, in and out through the instrument receiving portion along the instrument longitudinal axis, and rotated around its own shaft, i.e. around the instrument longitudinal axis. This aspect of the invention provides similar advantages as discussed above in relation to the previous aspects of the present disclosure.

It should be understood that the expression "middle portion" essentially corresponds to the second elongated portion as presented above. Correspondingly, the expression "instrument receiving portion" essentially corresponds to the first elongated portion as presented above.

The device further may comprises an actuator, denoted in the following as a first actuator, mounted in the base portion to provide force feedback to a user when rotating the instrument around the first axis (A), and a second actuator mounted in the middle portion to provide force feedback to a user when rotating the instrument around the second axis (B), as well as an additional actuator, denoted in the following as a third actuator, mounted in the middle portion to provide force feedback to a user when moving the instrument in and out of the instrument receiving portion, i.e. along the instrument longitudinal axis (C). Furthermore, the device may also comprise a fourth actuator mounted in the instrument receiving portion and adapted to provide force feedback to the user when turning the instrument around its own shaft, i.e. around the instrument longitudinal axis (C).

It should be noted that the second actuator, as an alternative, may be mounted in the base portion for providing force feedback to the user when rotating the instrument around the second axis (B), e.g. via a transmission.

The present disclosure solves the tracking and actuating in a different way than the existing solutions, which opens up the new features, as described above.

A pivot point exists where the first axis essentially crosses the second axis. In the present disclosure, the instrument representation pass the pivot point, and more specifically the said second axis, slightly offset of it. The offset is needed to fit an actuating wheel against the instrument representation shaft. The instrument shaft can for instance be implemented as threaded rod, a square shaft with a rack on one side, a round rack with gears around the shaft, or as a smooth cylinder. The actuating wheel that drives and tracks the instrument representation shaft lengthwise along the instrument longitudinal axis (C), can be a straight gear, a slightly angled gear or a friction wheel. The actuating wheel is driven either directly or preferably via a transmission by the said third actuator. Since the third actuator is mounted in the middle part, and preferably coaxial with the first axis, the third actuator and the transmission will follow only the movements around the first axis (A), and not by movements around the second axis (B). This will give a design that has a minimum of mechanics that is moving together with the instrument receiving portion, which enables placement of the haptic interface devices close to each other.

The second axis (B) is actuated by the said second actuator, which can be mounted in the middle portion. If the second actuator is mounted behind and in-line of the third actuator, and also preferably coaxial with the first axis (A), it will form an oblong middle portion. To make this possible, a transmission from the second actuator to the instrument receiving portion is arranged, making the instrument receiving portion move around the second axis when the second actuator actuates. Furthermore, if the first actuator that actuates the first axis is mounted on the base, behind the middle portion, also coaxial with the first axis, the whole haptic interface device becomes oblong, where the first, the second and the third actuator lies in a row and is essentially perpendicular to the entry path of the instrument receiving portion, when the instrument receiving portion is at its zero angle.

The mentioned design opens for having considerably higher deflection angles around the first and the second axis, and the format of the interface device becomes narrow and thereby gives the possibility to place several interface devices close to each other. The design with the third actuating gear opens the possibility to decouple the instrument representation from the instrument receiving portion and since the third actuator is placed in the middle portion and concentric with the first axis, it will not move along with the instrument receiving portion when the instrument is moved around the first or the second axis. This gives a narrow mechanical design around the pivot point, which in combination with the narrow design in total gives the possibility to place portals close to each other without mechanical interference between them.

In addition, the present disclosure allows for the additional implementation of an instrument detection and identification functionality, using a detector adapted for determining an identity of the instruments based on an identification pin comprised with a tip of the instrument shaft.

Furthermore, the haptic user interface device preferably forms part of a surgical simulation system, further comprising a processing unit arranged in communication with the haptic user interface device and adapted to execute simulation software for simulating a surgical procedure, wherein the control unit is adapted to control an actuator of the at least one haptic user interface device based on the surgical procedure. The surgical simulation arrangement will be further discussed below in relation to the detailed description of the present disclosure.

Further features of, and advantages with, the present disclosure will become apparent when studying the appended claims and the following description. The skilled addressee realize that different features of the present disclosure may be combined to create embodiments other than those described in the following, without departing from the scope of the present disclosure.

BRIEF DESCRIPTION OF THE DRAWINGS

The various aspects of the present disclosure, including its particular features and advantages, will be readily understood from the following detailed description and the accompanying drawings, in which.

DETAILED DESCRIPTION

Figure 1:
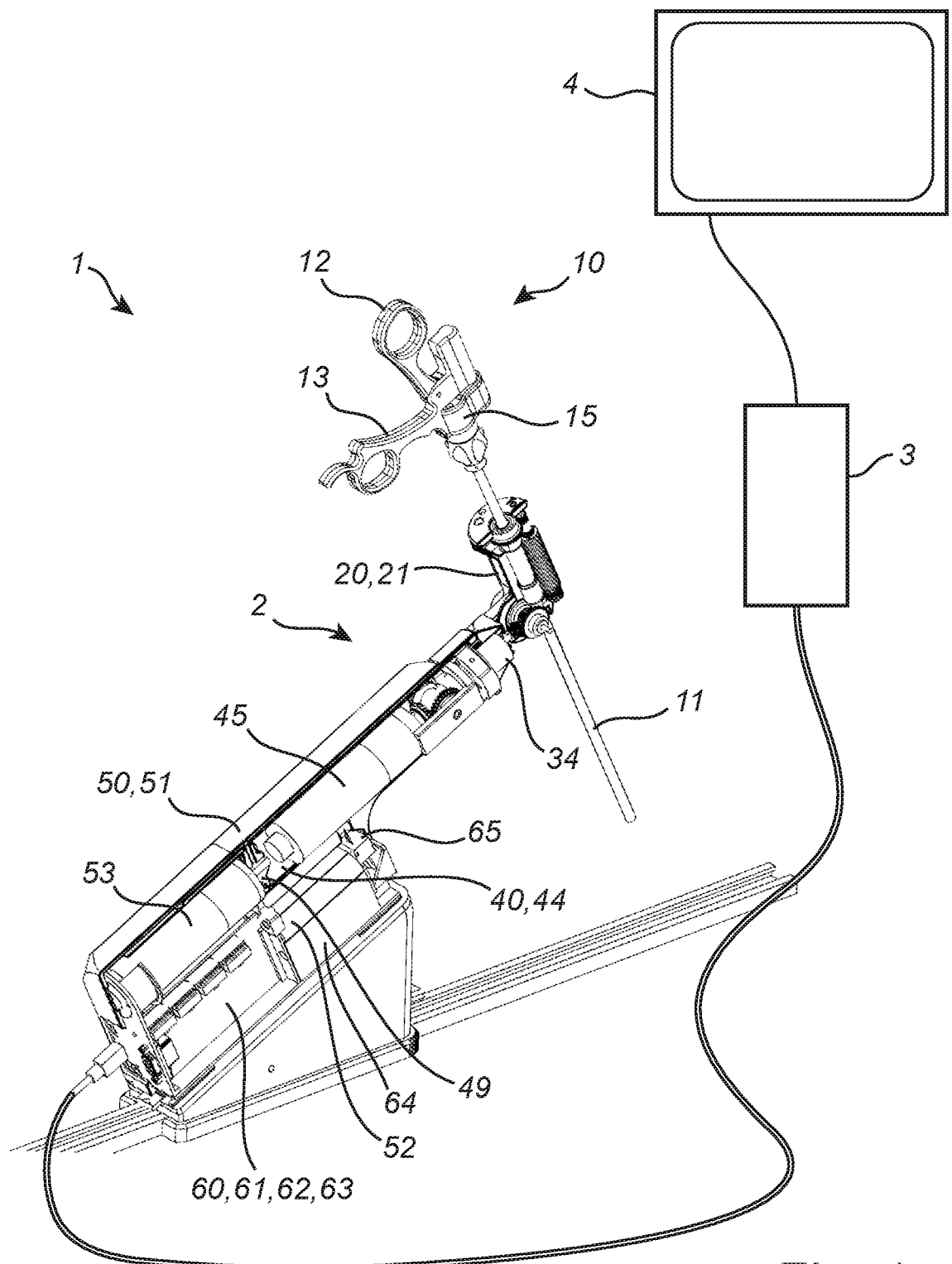
FIG. 1 is a schematic view of a surgical simulation system with a user interface device according to an embodiment of the present disclosure.

The present disclosure will now be described more fully hereinafter with reference to the accompanying drawings, in which currently preferred embodiments of the present disclosure are shown. This present disclosure may, however, be embodied in many different forms and should not be construed as limited to the embodiments set forth herein; rather, these embodiments are provided for thoroughness and completeness, and fully convey the scope of the present disclosure to the skilled addressee. Like reference characters refer to like elements throughout.

The System

With reference to FIG. 1, the simulation system (1) comprises a processing unit (3) running simulator software for simulating a surgical procedure, and a display (4) for displaying a visualization of the simulated procedure to the user. The interface device (2) (also referred to above as a surgical simulation arrangement) is connected to the simulation system (1), and allows a user to provide input to the system (1), thereby interacting with the simulation visualized in the display device (4). The user interface device (2) gives the user the possibility to insert an instrument representation (10) into the instrument receiving portion (20) of the user interface device (2) and then manipulate the instrument (10) in the mentioned four degrees of freedom. The user interface device (2) detects the presence of the instrument representation (10) and identifies it.

In the described embodiment, the user interface device is haptic, i.e. it is adapted to provide a user with force feedback in all four degrees of freedom. The interface device can also be non-haptic in any or all of the degrees of freedom, where it only tracks the motion without providing force feedback.

Description of the Instrument

The instrument representation (10) disclosed in FIG. 1 comprises a handle (12) and a rigid shaft (11). The handle can be a real handle used in surgical procedures, or it can be a mockup of a real handle. Any kind of handle for the applicable surgical procedures can be mounted on the shaft, such as, but not limited to, a grasper, a scissor, a clip applier, a laparoscope. The instrument handle (12) often has an additional degree of freedom for the user such as a grip portion (13) for a scissor-like handles or a turning motion of the laparoscope camera (not depicted here). The additional degree of freedom for a handle used in a simulator is tracked with a sensor. In FIG. 1, the grip portion is tracked with a grip sensor (15). Furthermore, the handle (12) can be equipped with an actuator to provide force feedback. Neither the tracking of the handle nor the force feedback mechanism is described further in this context, but is only mentioned as an orientation in the art of surgical simulation.

Many instrument handles also give the user the freedom to turn the shaft to a relaxing working position, to avoid using his or her wrist. This is done by using his or her finger and twisting a knob (14) which turns the shaft. This mechanism is also not part of the present disclosure and is not described further.

The shaft of the instrument (11) is a rigid shaft that corresponds to the real shaft of a real instrument. The shaft is mounted, just like the real shaft, below the mentioned turning knob of the real or mockup instrument.

Figure 4:
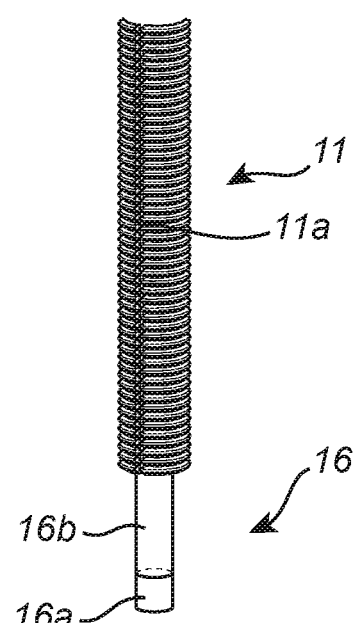
FIG. 4 illustrates details of the instrument shaft and identification system according an embodiment of the present disclosure.

The preferred embodiment of the rigid shaft is illustrated in FIG. 4, and is a threaded shaft (11) with a thread that has a pitch and teeth angle that can mate with a gear wheel (35), preferably but not limited to a standard thread and a standard gear wheel. The purpose of the gear wheel is explained further down. It is noted that the shaft can, as an alternative, have straight gears, like a circular rack, also engaging a gear wheel. The shaft can also be a smooth cylindrical shaft that mates with a friction wheel instead of a gear wheel. If the rotation around the above mentioned instrument longitudinal axis (C) degree of freedom is omitted in the implementation of the instrument receiving portion, the shaft can also be a rectangular rod with a rack on one side that engages a gear wheel.

Furthermore, the rigid shaft has two cut grooves (11a) along its length, allowing for the mechanism inside the instrument receiving portion (20) to track and provide force feedback to the instrument shaft in (11) the rotation direction around the instrument longitudinal axis (C). It is noted that there can also be one or more than two grooves in the rigid shaft.

Figure 3:
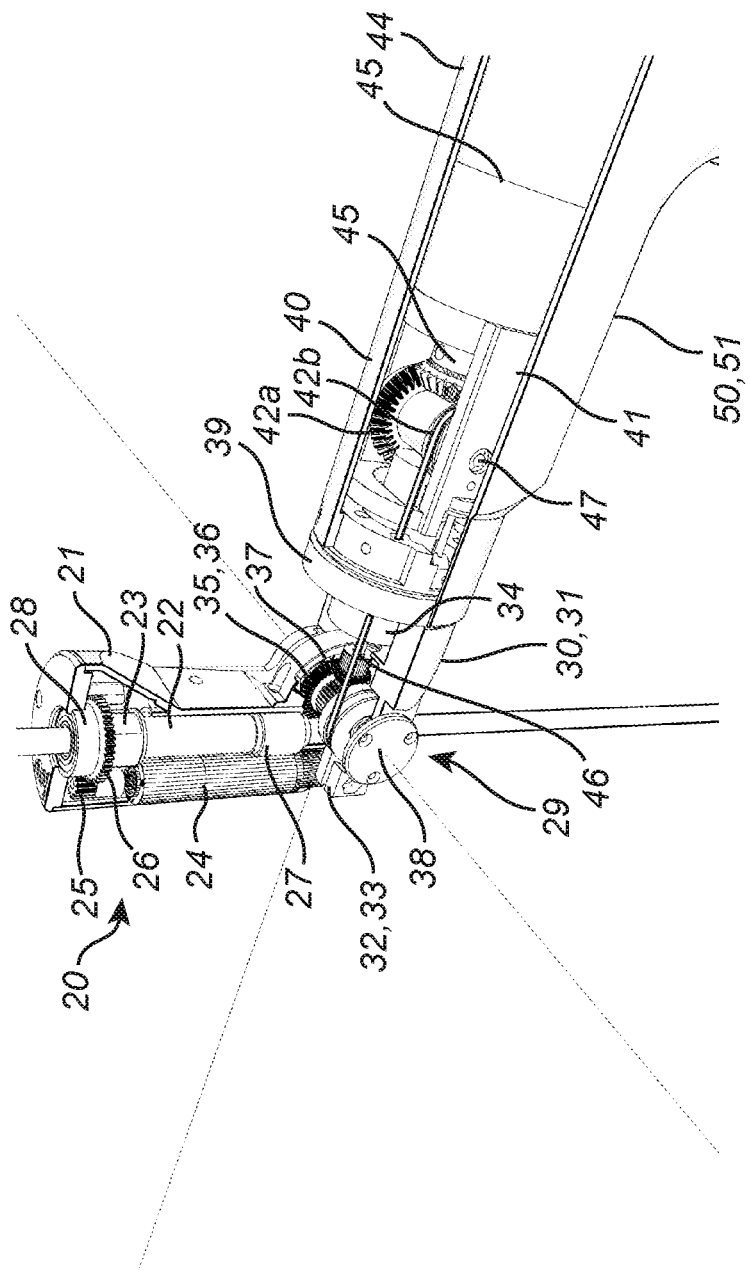
FIG. 3 illustrates details of the user interface device according to an embodiment of the present disclosure.

Description of the Instrument Receiving Portion and the Rotation Around the Instrument Longitudinal Axis (C) Degree of Freedom The following is described mainly with reference to FIG. 3, which discloses details of the preferred embodiment. The instrument representation (10) with its rigid shaft (11) can be inserted into an instrument receiving portion (20). A suspended sleeve (22) inside the instrument receiving portion suspends the instrument shaft in the instrument receiving portion, allowing the instrument to move in and out of the instrument receiving portion and to rotate around its axis, i.e. around the instrument longitudinal axis (C).

The suspended sleeve (22) is supported in the instrument receiving portion housing (21) by an upper and lower bearing, the upper is a ball bearing (28) and the lower is a sliding bearing (27) or a low profile ball bearing. A locking key (23) arranged in the suspended sleeve, engages the groove (11a) in the rigid shaft (11) and locks the suspended sleeve to the instrument shaft rotation wise. The locking key (23) is spring loaded by a locking ring so that the instrument can be inserted into the suspended sleeve without consideration to the orientation of the locking key with respect to the groove in the instrument shaft. When the user turns the instrument, the locking key will eventually snap into one of the grooves (11a) and lock the sleeve (22) to the instrument shaft (11).

The rotary motion of the sleeve and the rotationally locked-on instrument shaft is transferred to the said fourth actuator (24) via a gear transmission (25+26). The fourth actuator (24) is an electrical motor with a rotary encoder so that the rotational position of the sleeve and instrument can be tracked and so that the torque from the motor can be transferred to the sleeve and, via the locking key, to the instrument. This arrangement provides the user tracking and force feedback to the instrument rotation wise, i.e. around the instrument longitudinal axis (C). It is noted that the transmission between the sleeve and the motor can be solved in other ways, one example being a belt transmission. It is also noted that the electrical motor can be omitted if force feedback is not desired in this degree of freedom. A rotary encoder or another sensor, such as a potentiometer, is still needed to track the rotation of the instrument.

As mentioned above, an alternative implementation, although not preferred, of the present disclosure can be to use a rectangular shaft with a rack on one side, and thus omit the instruments rotary degree of freedom in the mechanism in the instrument receiving portion. In such case, the rotationally suspended sleeve is then instead fixated in the instrument receiving portion housing (21) or the sleeve can be implemented as an integral part of the housing structure.

Description of the Movement Along the Instrument Longitudinal Axis (C) Degree of Freedom When the instrument shaft (11) reaches the distal end of the instrument receiving portion (20) it will be engaged by the mentioned gear wheel (35), which will transform the lengthwise motion, i.e. along instrument longitudinal axis (C), of the instrument into a turning motion of the gear wheel (35). The gear wheel revolves on a shaft which is concentric with the said second axis (B). This means that the instrument shaft (11) passes slightly off-center with respect to the pivot point, i.e. the crossing between the said first axis (A) and the said second axis (B). The off-center distance is determined by the sum of the pitch radius of the gear wheel (35) and the mating pitch radius of the threaded or geared shaft (11). Since the gear wheel radius is relatively small and so is the instrument radius, the off-center distance is relatively small and judged to be negligible and not disturbing for the user. In a real surgical procedure, the pivot point is determined by the different layers of tissues in the specific perforation of a specific patient's body, so the pivot point is not distinct or known anyway.

As mentioned, the lengthwise movement along the instrument longitudinal axis (C) of the instrument will create a rotary motion of the gear wheel (35). This rotary motion is transferred to the said third actuator (34) via a gear transmission (36+37). The gear wheel is joined with an angled gear (36) which mates with a pinion gear (37) mounted on an electrical motor shaft, which together with a rotary encoder forms the third actuator (34). The third actuator can now track the motion of the instrument lengthwise and provide force feedback to that degree of freedom, i.e. along the instrument longitudinal axis (C).

The motor is mounted in a housing (31) in the distal end of the middle portion (40) and concentric with the first axis (A). The motor will therefore not follow the movement of instrument receiving portion (20), which has the benefit that the instrument receiving portion (20) can be made small, comparably to the size of a real 12-mm port used in real surgery, and that the moving structures around the pivot point is kept to a minimum. Also, since the motor is concentric with the first axis (A) it will not add any imbalance weight to this degree of freedom. However, it is noted that the present disclosure does not exclude an alternative positioning of the motor, although it is judged that the preferred position of the motor is the most beneficial, for the reasons explained above.

Description of the Instrument Detection and Identification

Figure 2:
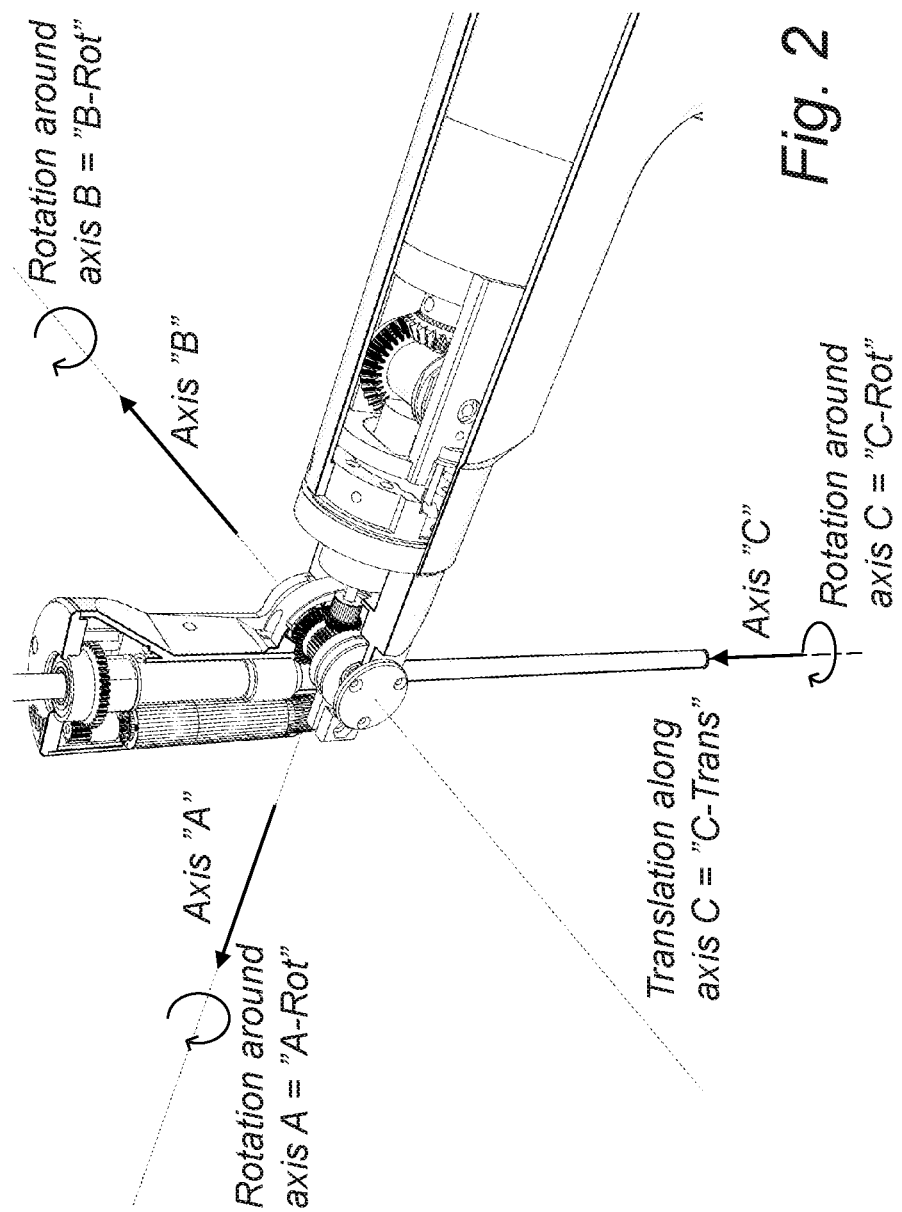
FIG. 2 illustrates the degrees of freedom for the instrument shaft.

The following description is made mainly with reference to FIG. 2 and FIG. 3, which disclose details of the currently preferred embodiment of the present disclosure.

As the instrument shaft (11) travels down through the instrument receiving portion (20), a slotted optical sensor (29) detects the presence and the identity of the instrument shaft (11). By this time, the shaft has already engaged the gear wheel (35) and the encoder in the motor has started to provide information about the instruments travel length along the instrument longitudinal axis (C). At the tip of the instrument shaft (11), a cylindrical pin is mounted, hereby referred to as an identity pin (16). The identity pin is partly transparent (16b) and has a certain length. Different instrument shafts can be fitted with different identity pins. The tip of the identity pin (16a) is painted to give an opaque section, which also can have a certain length. The identity of the instrument is determined by the total length of the identity pin (16), and optionally also the length of the opaque tip (16a). The slotted optical sensor (29) consists of an infrared light emitting diode (LED), an air gap and a photoelectric transistor. When the air gap is open or closed, the photoelectric transistor receives or doesn't receive the light from the LED, thus giving a signal that reflects the state of being occluded or not occluded. As the instrument with its identity tip passes through the slotted optical sensor it will first be occluded by the painted opaque tip, then be not occluded by the transparent part of the identity tip and finally be occluded again by the instrument shaft. By using the slotted optical sensor (29) in combination with the rotary encoder in the motor (34), the total length of the identity tip (16) and the length of the opaque part (16b) of the identity tip can be measured. By using either any one of the lengths or a combination of the two, the specific identity of the tip and the shaft (11) can be determined.

With the above described identification solution, the user can pick up one of several instruments from a table and insert in into one of several user interface devices without explicitly telling the system first. The user interface device chosen for insertion by the user will then detect and identify instrument chosen by the user. In the simulation software (3), the information can now be used to render and simulate that specific instrument appearance and behavior without the need for an explicit selection from the user. This feature significantly improves the user's ability to interact with the system (1) in a more realistic manner. A simulation of a certain surgical procedure can be prepared by associating a number of instruments with a specific instrument identity numbers respectively. When this is done, the user doesn't need to make any instrument selections during the exercise, but only focus on picking the right instrument from a set of instruments, either according to instructions from the simulation system, or according to his or her own choice for the most suitable instrument for a particular procedure step.

Another aspect of the abovementioned instrument identification feature is that the user can train on elements of instrument handling that hasn't been possible before. One example is when the user holds a tissue with one instrument and then needs to change the second instrument during a critical phase of the procedure. One hand is then occupied with a critical task and the other hand needs to perform a retraction movement, switching instrument, and the inserting the new instrument to finally reach roughly the same region in the body without colliding and harming other organs or tissues.

Description of the Rotation Around the Second Axis (B) Degree of Freedom

The instrument receiving portion (20) is suspended on the middle portion (40) with a first shaft (38), allowing the instrument receiving portion to be rotated around the second axis (B) with respect to the middle portion. The first shaft (38) is the same shaft as the gear wheel (35) revolves on. The rotational movement of the instrument receiving portion (20) around the second axis (B) is transferred to the said second actuator (45) via a transmission comprising a carrier wheel (32), a belt (46), a pulley wheel (42a) and a bevel gear (42b). The carrier wheel (32) is suspended on the first shaft (38) and has a rectangular protrusion that mechanically connects the carrier wheel (32) to the instrument receiving portion housing (21) making them move together in the movement around the second axis (B). The belt (46) is clamped in the carrier wheel (32) and transfers the motion from the carrier wheel (32) to the pulley wheel (42a). The belt can advantageously be a fiber rope that allows bending and still has a tensile strength comparable to a steel wire in order to transfer the relatively high forces from the second actuator (45).

The pulley wheel (42a) is joined with a first bevel gear (42b) and suspended by a second shaft (47). The belt (46) is fixated on the pulley (42a) at one point to avoid slipping. The first bevel gear (42b) mates with a second bevel gear (43) which is mounted on the shaft of the second actuator (45). The actuator is mounted inside the middle portion (40) concentric with said first (A), and in line with the third actuator (34). Again, this is a design that gives the smallest possible structure around the first axis (A) and no imbalance and a minimum inertia contribution to the rotational movement around the first axis (A).

A rotary encoder inside the second actuator (45) is used for tracking the motion. The arrangement provides motion tracking and force feedback to the user for rotary motions around the second axis (B).

The belt (46) can stretch over time and an arrangement for tensioning the belt is preferable. This is implemented by having a floating cage (41) on which the said second actuator (45) is mounted and in which the transmission to the one side of the belt transmission (42+43) is mounted. The cage (41) is spring loaded from the distal end of the middle portion (30), which tensions the belt. To avoid the cage (41) to spring back when force feedback is applied to the second axis (B), a ratcheting mechanism is implemented, allowing the cage to move in a direction that tensions the belt, but not in the opposite direction. This ensures that the belt transmission (34) is free from slack and doesn't spring back when torque is applied by the second actuator. An alternative solution is to have a tension screw that acts on the cage assembly (41+42+43+45) and thus tensions the belt. However, such solution increases the need for manual inspection and adjustments and an automatic adjustment mechanism is preferable.

It is noted that a belt transmission other than the described fiber rope can be used. One example is a standard timing belt drive and teethed drive wheels. A second example is to use a chain and sprockets. A third example is to use a steel wire and suitable pulleys.

Description of the Rotation Around the First Axis (A) Degree of Freedom

The middle portion (40) has a tubular shape and is rotatably suspended inside the base housing (51) to provide a rotary motion around the first axis (A) with respect to the base (50). The middle portion (40) is suspended by a bearing (48) in the distal end of the base housing (51) and by the shaft of a first actuator (53), which is mounted with a motor mount (52) on a wall inside the base housing (51). A rotary encoder inside the first actuator (53) tracks the motion. The arrangement provides tracking and force feedback to the user around the first axis (A) with respect to the base (50). The first actuator (53) is mounted concentric with the first axis (A) and in line with the second (34) and third actuator (45). Since the first actuator (53) doesn't move with any of the degrees of freedom, the benefits in terms of imbalance and inertia mentioned for the second and third actuator does not apply here. Instead, the benefit for placing the first actuator in line with the second and third actuator is to give a design that is narrow and oblong. An alternative solution is to place the actuator above or below the middle portion, to give a shorter interface device. However, then the control unit, described below, needs to be repositioned and the advantage of such alternative might be lost.

Maximum Angular Deflection of the Rotation Around the First Axis (A) and the Second Axis (B) Degrees of Freedom The described arrangement, where the first, second and third actuators are lined up, gives the interface device a narrow design, and a minimum amount of space needed around the pivot point for the movements. An implicit advantage of this, combined with the slightly offset instrument longitudinal axis (C) with respect to the second axis (B), is that the maximum angular deflection is much improved in comparison to known haptic interface devices. The movement around the second axis (B) is +/−60° (compared to +/−45° on other interface devices). The movement around the first axis (A) is +/−75° (compared to +/−45° on other interface devices). This extra angular deflection provides a further flexibility when preparing a procedural setup.

Description of the Control System

The control system (60) for the force feedback system comprises a central processing unit card (61), a motor power card (62), an encoder counting card (63) and a battery pack (64). All signals to and from the abovementioned sensors and motors (actuators) are handled by the control system (60). It is noted that the electrical implementation of the control system can be made in many different ways by combining or separating functions and thus changing the number of needed electronic boards. The control system (60) is connected to the simulation computer (3) with a serial interface cable such as Ethernet, USB, Firewire, Thunderbolt, USB-C, RS232, RS422, RS485, CAN, CANopen, EtherCAT, Profibus, Industrial Ethernet or other standard serial interfaces. The interface device could also connect to the simulation computer (2) via WiFi, Zigbee, Bluetooth or any standard wireless standard.

The battery pack (64) provides a high current to the motors, which is needed intermittently at high torque outputs. A high current external power supply is therefore not needed, which is an advantage in terms of lower weight and the absence of thick power cables and large power supplies. Another advantage of the battery is that it can absorb the backdrive currents which often is generated in force feedback systems. The power consumption of the motors and the control unit is low on average so the battery pack (64) can be charged with a relatively small current and still maintain its capacity. The charging can preferably be made from power supplied by the serial interface, e.g. from the USB power supply or from a Power over Ethernet (PoE) supply. Other serial interfaces also provide power, such as Firewire, Thunderbolt, USB-C etc. In this way, the amount of cables connected to the user interface device can be kept to a minimum. It can also be charged by an external adapter or a separate power supply. An alternative to the mentioned charging is to have a wireless charging system, where the charging current is induced by coils instead. In combination with a wireless communication system, the user interface device would need no connecting cables.

Description of the Calibration System

The mentioned encoders in the mentioned actuators for tracking angles and positions are incremental, and the control system (60) needs to have reference positions to convert the incremental positions to absolute positions. For the rotation around the first axis (A) degree of freedom, a reference point is created when the instrument is crossing the center angle. This is accomplished by having a reflective optical sensor (65) inside the base housing (51). The tubular structure (44) of the middle portion (40) is painted, at the location of the optical sensor, with a matt dark color and a bright specular color and the transition between the two painted surfaces is at the center angle of the middle portion (40, 44). The reflective optical sensor (65) will measure the transition between the two painted areas. The signal from the reflective optical sensor (65) is connected to the control system (60), which resets the yaw angle when the signal transition is read.

It is noted that the solution for calibrating the rotation angle around the first axis (A) can be made differently, e.g. by having a magnet and a Hall Effect sensor that senses a polarity change. It can also be a potentiometer giving an absolute position, an absolute position encoder, a light detector sensing a light source inside the middle portion etc.

The calibration of the motion along the instrument longitudinal axis (C) of the instrument shaft (11) has been mentioned above, where the slotted optical sensor (29) detects both the tip of the identity pin (16) and the tip of the instrument shaft (11). When the tip of the shaft is detected, the absolute position is known and the calibration is done.

The rotation angle around the second axis (B) is calibrated by letting the user move the instrument (10) back and forth to find the both end positions of the mechanism. The center angle is then calculated as the average of the two end positions. An alternative and preferred solution is to introduce a sensor also for this movement. This can e.g. be made by having an optical sensor, magnetic sensor or potentiometer measuring the angle of either the instrument receiving portion directly or the belt drive pulley which is connected to the instrument receiving portion.

A calibration of the rotation angle around the instrument longitudinal axis C of the instrument shaft is judged to be unnecessary since the orientation of the round shaft is not easily seen anyway. The preferred implementation of the calibration of the orientation angle is to set it to zero when the instrument tip is detected in the slotted optical sensor (29).

Description of an Adjustable Base

Figure 5:
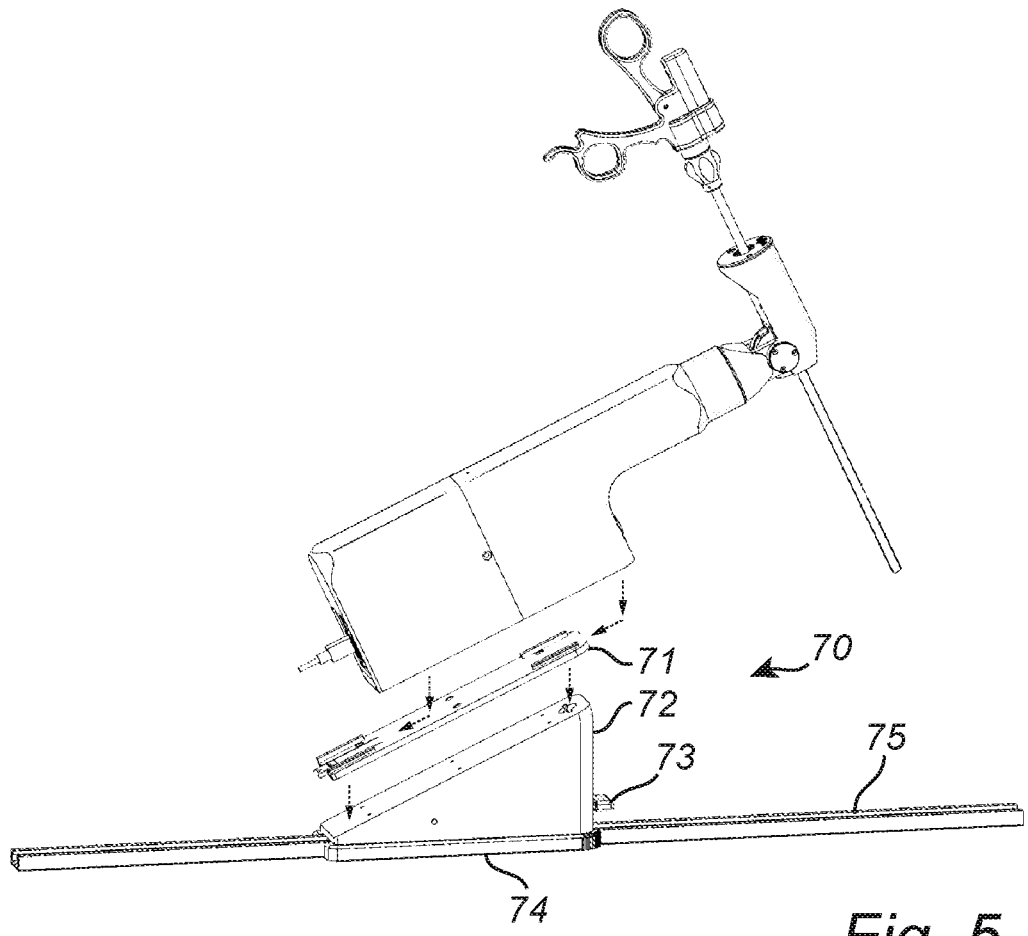
FIG. 5 illustrates details of the fastening and positioning system according to an embodiment of the present disclosure.

The user interface device (2) described above is a unit that can be mounted directly on any kind of base structure, which can be grounded, movable or adjustable, that implements an adequate setup for a certain simulator training. It can e.g. be mounted on a table, on a stand, inside a workstation box, inside a manikin etc. In the preferred embodiment, which is disclosed in FIG. 5, a quick connector plate (71) is used to enable a mechanical connect and disconnect between the quick connector plate (71) and the user interface device (2) without the need for tools. The quick connector plate (71) is mounted on a grounded, movable or adjustable structure with screws and the user interface device (2) can then snap on the quick connector place (71).

Furthermore, the preferred embodiment of the base structure for e.g. laparoscopic or thoracoscopic procedures is to have sleds (72) that can be adjusted along a rail (75) and to have a number of rails next to each other and one or several sleds placed on each rail. The rails (75) are mounted on a base structure, e.g. a plate, a table or a workstation. A sled (72) is mounted on a rail (75) by having a brake bad (74) and a spring-loaded lever (73), where the brake pad fits in profile of the rail so that the brake pad can hold down the sled against the base structure. The user presses the spring-loaded lever (73) to release the brake (74), allowing him or her to change the position of the sled along the rail. On top of the sled, a quick connector plate (71) is mounted, and a user interface device (2) can thereby be easily mounted on the sled. The solution with the plate, the rails, the sleds and the quick connectors gives the user or the simulator vendor a range of possibilities to compose a training platform for many kinds of surgical procedures.

Figure 6A:
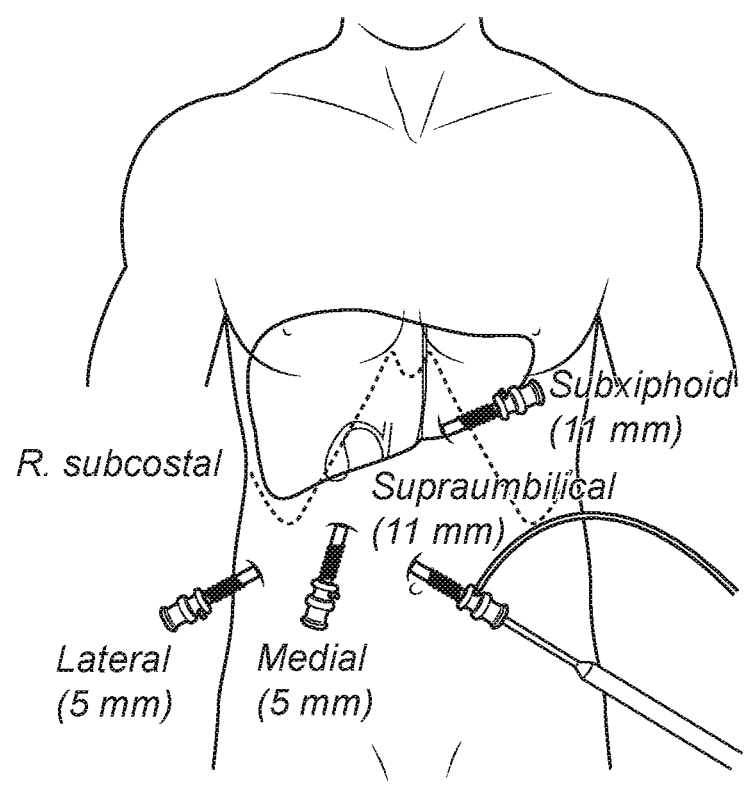
FIGS. 6a and 6b illustrates a comparison between a real simulation setup for a laparoscopic cholecystectomy procedure and the corresponding setup of multiple user interface devices according to an embodiment of the present disclosure.
Figure 6B:
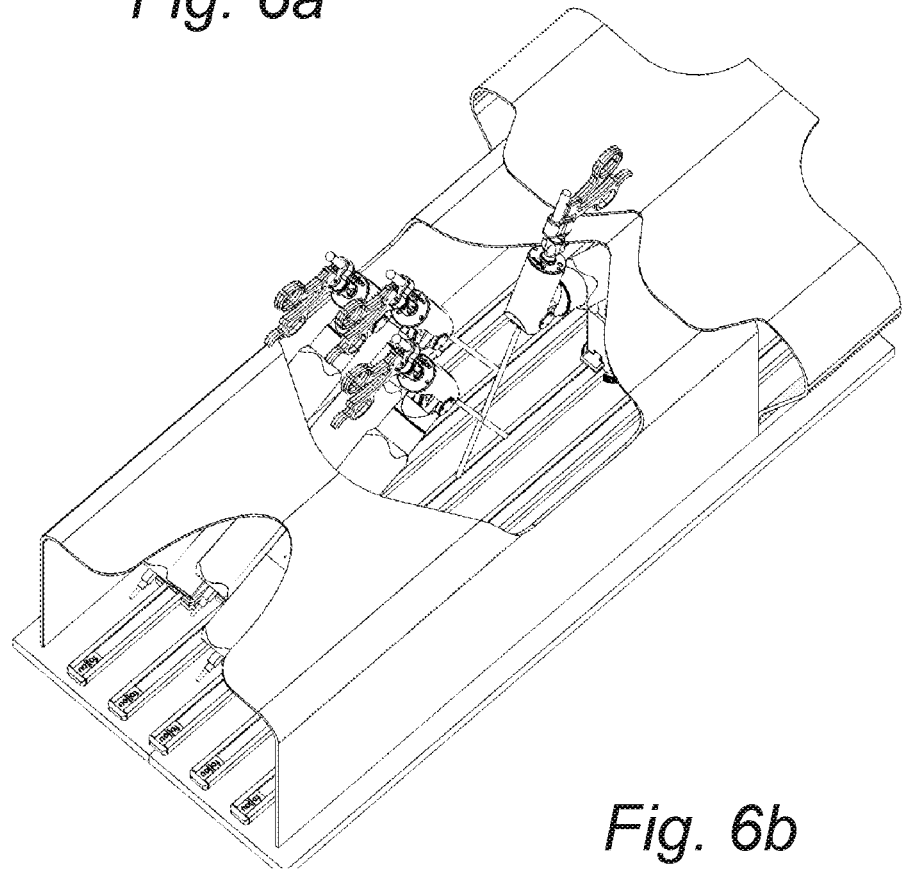

FIG. 6a shows the setup for a real surgical procedure, in this case a laparoscopic cholecystectomy, and FIG. 6b shows a setup with a set of user interface devices, as described and disclosed in the present disclosure, forming the surgical simulation system. The simulation setup in FIG. 6b also comprises a stylistic manikin with natural dimensions to give a size reference. The figures show that this particular simulator procedure can be mimicked, but this is judged to be the case also for all laparoscopic procedures based on studies. The same applies also for e.g. thoracoscopic procedures and arthroscopic procedures in the shoulder and in the knee.

The control functionality of the present disclosure may be implemented using existing computer processors, or by a special purpose computer processor for an appropriate system, incorporated for this or another purpose, or by a hardwire system. Embodiments within the scope of the present disclosure include program products comprising machine-readable medium for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a sequence the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps. Additionally, even though the present disclosure has been described with reference to specific exemplifying embodiments thereof, many different alterations, modifications and the like will become apparent for those skilled in the art.

In addition, variations to the disclosed embodiments can be understood and effected by the skilled addressee in practicing the present disclosure, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A surgical simulation arrangement for a user handling a simulation instrument, the surgical simulation arrangement comprising:
    a first elongated portion extending along an instrument longitudinal axis and having a proximal and a distal end, the first elongated portion provided with an instrument passage extending from the proximal to the distal end of the first elongated portion and adapted for receiving a shaft of the simulation instrument, wherein the instrument passage is adapted to allow the shaft of the simulation instrument to move longitudinally through the instrument passage,
    a second elongated portion extending along a first axis and having a first and a second end, and
    a joint arrangement adapted to pivotally connect the distal end of the first elongated portion with the first end of the second elongated portion,
    wherein the instrument passage is positioned in a direction away from the second elongated portion and offset in relation to the joint.

2. The surgical simulation arrangement according to claim 1, wherein the instrument passage is arranged within the first elongated portion.

3. The surgical simulation arrangement according to claim 1, further comprising the simulation instrument.

4. The surgical simulation arrangement according to claim 1, further comprising a first actuator mounted in a base portion of the surgical simulation system and adapted to provide force feedback to the first axis.

5. The surgical simulation arrangement according to claim 1, further comprising a second actuator arranged within the second elongated portion and adapted to control an amount the first elongated portion is allowed to pivot in relation to the second elongated portion and the joint arrangement.

6. The surgical simulation arrangement according to claim 1, further comprising a third actuator arranged within the second elongated portion and adapted to engage with the shaft of the simulation instrument for controlling a longitudinal movement of the shaft of the simulation instrument through the instrument passage to provide a second force feedback to the user operating the simulation instrument.

7. The surgical simulation arrangement according to claim 1, further comprising a fourth actuator arranged within the first elongated portion and adapted to engage with the shaft of the simulation instrument for controlling a rotation of the shaft of the simulation instrument to provide a first force feedback to the user operating the simulation instrument.

8. The surgical simulation arrangement according to claim 1, wherein the shaft of the simulation instrument comprises a threaded portion.

9. The surgical simulation arrangement according to claim 1, further comprising a locking key arranged at the instrument passage and adapted to engage with a groove extending along a length of the shaft of the simulation instrument.

10. A haptic user interface device for a surgical simulation system, the arrangement comprising:
a frame having a fixed base,
a middle portion, rotatable around a first axis in relation to the base,
an instrument receiving portion extending along an instrument longitudinal axis and rotatable around a second axis in relation to the middle portion, the second axis being essentially perpendicular to the first axis,
an instrument having a shaft suspended by the instrument receiving portion so as to be pivotable around the first axis and the second axis, and where the instrument longitudinal axis is essentially perpendicular to the second axis and offset with respect to the second axis, and
a third actuator comprising an actuating wheel arranged to provide force feedback to a user of the surgical simulation system when moving the instrument along the instrument longitudinal axis and where the actuating wheel is concentric with the second axis.

11. The device according to claim 10, wherein the instrument shaft is a cylindrical threaded or geared shaft engaging the actuating wheel.

12. The device according to claim 10, wherein the instrument is a rectangular shaft with a rack on one side which engages the actuating wheel.

13. The device according to claim 10, wherein the instrument shaft is a cylindrical smooth shaft and the actuating wheel is a friction wheel.

14. The device according to claim 10, wherein a first actuator is arranged within the middle portion.

15. The device according to claim 10, wherein the frame comprises a fourth actuator arranged within the instrument receiving portion arranged to provide force feedback to the instrument around the instrument longitudinal axis.

16. The device according to claim 10, wherein the frame comprises a second actuator mounted in the middle portion and arranged to provide force feedback to the second axis.

17. The device according to claim 10, wherein the frame comprises a first actuator mounted in the base portion and arranged to provide force feedback to the first axis.

18. The device according to claim 10, wherein the frame comprises a second actuator mounted in the base portion and arranged to provide force feedback to the second axis.

19. The device according to claim 10, further comprising an optical detector arranged in the instrument receiving portion and adapted to provide a detection of the presence of an instrument and to provide a calibration point of the instrument tip position for the encoder in the actuator for the longitudinal force feedback.

20. A surgical simulation system, comprising:
at least one haptic user interface device according to claim 10, and
a processing unit arranged in communication with the at least one haptic user interface device and adapted to execute simulation software for simulating a surgical procedure,
wherein the control unit is adapted to control an actuator of the at least one haptic user interface device based on the surgical procedure.

* * * * *